United States Patent [19]
Kim et al.

[11] Patent Number: 5,776,460
[45] Date of Patent: Jul. 7, 1998

[54] PROCESSED GINSENG PRODUCT WITH ENHANCED PHARMACOLOGICAL EFFECTS

[75] Inventors: Nak Doo Kim; Man Ki Park, 100-26 Nonhyun-dong, Kangnam-ku; Seung Ki Lee; Jeong Hill Park; Jong Moon Kim, all of Seoul, Rep. of Korea

[73] Assignee: Man Ki Park, Seoul, Rep. of Korea

[21] Appl. No.: 660,448

[22] Filed: Jun. 7, 1996

[30] Foreign Application Priority Data

Jun. 7, 1995 [KR] Rep. of Korea ............ 95-14973
May 23, 1996 [KR] Rep. of Korea ............ 96-17670

[51] Int. Cl.$^6$ ............................................ A61K 35/78
[52] U.S. Cl. ................................. 424/195.1; 514/25
[58] Field of Search ................... 424/195.1; 514/25

[56] References Cited

FOREIGN PATENT DOCUMENTS 62-158490  7/1987  Japan ............... C12P 19/00
92-5995    7/1992  Rep. of Korea ....... A23L 1/212

OTHER PUBLICATIONS

Japanese Laid–Open Patent Publication No. 62–158490 Statement of Relevancy.

Korean Patent Publication No. 92–5995 Statement of Relevancy.

*Primary Examiner*—Jean C. Witz
*Attorney, Agent, or Firm*—Burns, Doane, Swecker & Mathis, L.L.P.

[57] ABSTRACT

A processed ginseng product with enhanced pharmacological effects is provided due to a heat-treatment at a high temperature of 120° to 180° C. for 0.5 to 20 hours so as to make a ratio of ginsenoside $(Rg_3+Rg_5)$ to $(Rc+Rd+Rb_1+Rb_2)$ above 1.0.

3 Claims, 6 Drawing Sheets

Fig. 2-a
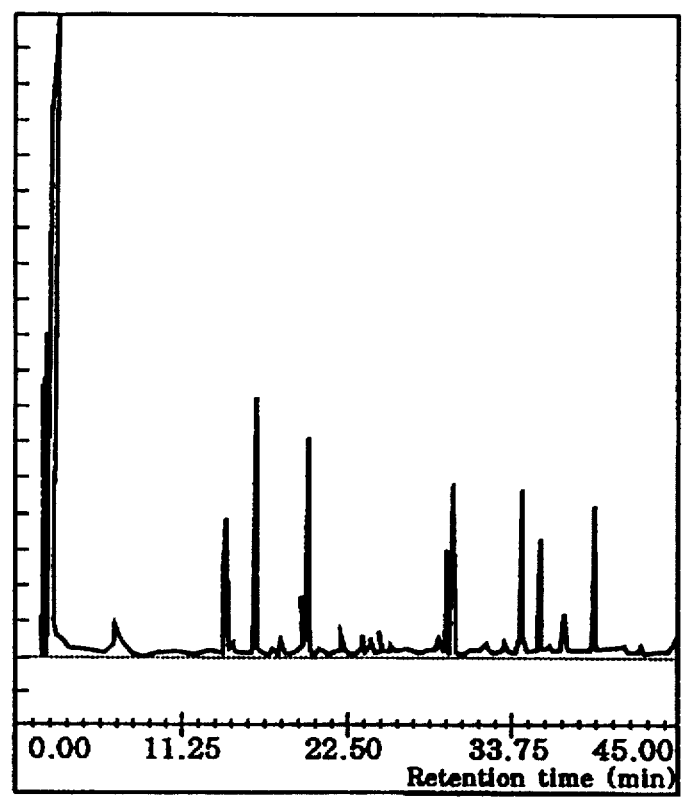

Fig. 2-b
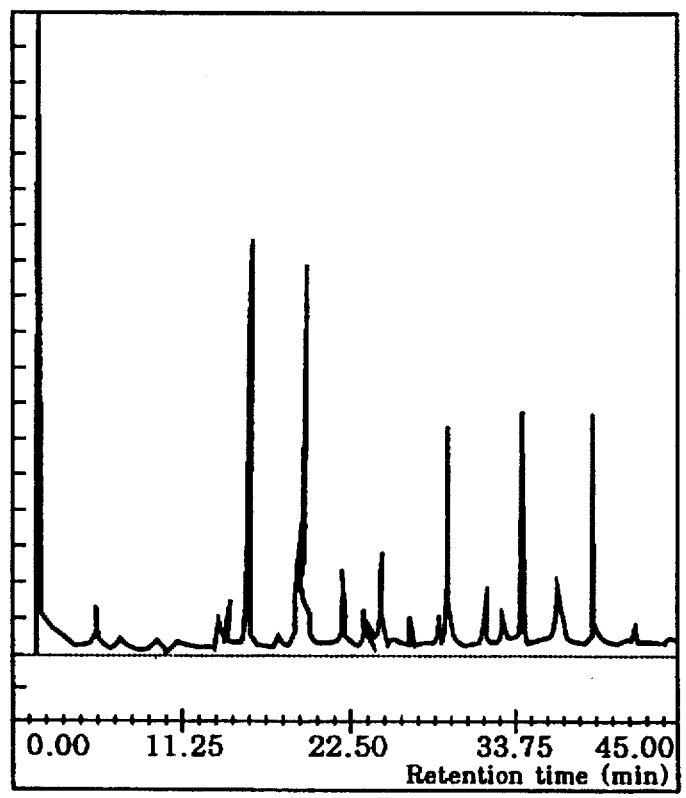

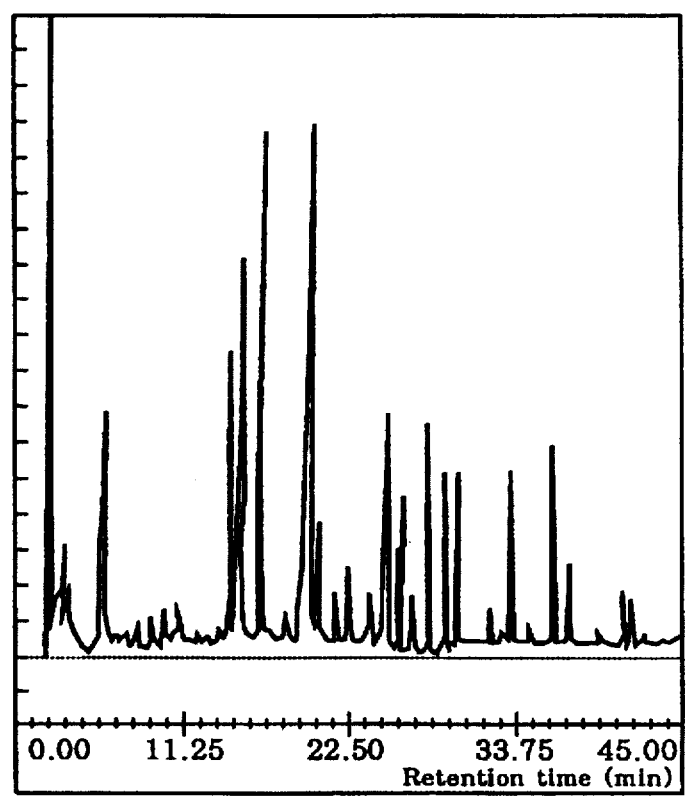
Fig. 2-c

PROCESSED GINSENG PRODUCT WITH ENHANCED PHARMACOLOGICAL EFFECTS

BACKGROUND OF THE INVENTION

Field of the Invention

The present invention relates to a processed ginseng product with enhanced pharmacological effects and to a drink composition containing the processed ginseng product. More particularly, the present invention relates to a processed ginseng product with enhanced pharmacological effects due to a heat-treatment of a ginseng at a high temperature of 120° to 180° C. for 0.5 to 20 hours so as to make a ratio of ginsenoside $(Rg_3+Rg_5)$ to $(Rc+Rd+Rb_1+Rb_2)$ of above 1.0, and to a drink composition containing the processed ginseng product.

Hitherto, a ginseng has been widely known as a representative nutritive tonic agent. Recently, various scientific studies on the chemical constituents and pharmacological effects of the ginseng have been reported so that the secret pharmacological effects are paid attention with modern scientific approaches. Until now, it has been known that the ginseng has various pharmacological effects such as prevention of aging, anti-arteriosclerosis, treatment of hyperlipidemia, treatment of hepatic insufficiency, improvement of liver function, protection of radiation injury, immune enhancement, improvement of cerebral function, anti-thrombotic, anti-stress, anti-diabetic, anti-hypertensive, anti-tumor effects, etc.

Generally, ginseng is used in the form of a fresh ginseng which is not dried yet, of a white ginseng which is prepared by drying the fresh ginseng at a normal temperature or of a red ginseng which is prepared by steaming and drying the fresh ginseng at a temperature of 98° to 100° C.

In particular, since pharmacological effects of a red ginseng are stronger than that of a white ginseng, the red ginseng has been recognized as a valuable medicine. In recent years, an intensive research regarding to trace components of the red ginseng has been performed, and interests in novel pharmacological effects of the trace components have been heightened. Such trace components which are produced by heat-treating during the preparation process of the red ginseng are evaluated as components which show excellent pharmacological effects of the red ginseng. Until now, the components known as present in only the red ginseng include saponin such as ginsenoside Rh2, Rs1, Rs2, Rg3. Rg2, Rh1, etc. and polyacetylene compound such as panaxytriol, and the like. Such compounds which are produced in course of preparing of the red ginseng are present in trace amounts.

The red ginseng is generally manufactured by steaming the fresh ginseng at 98° to 100° C. for about 2 hours. The quality of the red ginseng has been mainly evaluated by the appearance of the products. The red ginseng in which inner pore, crack, inner white portion, white bark, etc. are not present and which has a good red color and body shape, is classified as a high-grade red ginseng. Accordingly, in order to prepare the red ginseng for a better appearance, the process wherein the heating is performed at a lower temperature of below 98° C. was also investigated (Korean Patent Application Publication No. 5995/1992). As such, since commercial considerations put much emphasis on the appearance, the ginseng has not been heat-treated at a high temperature of above 100° C.

Recently, however, the process wherein a ginseng is heat-treated at a high temperature has been partially tried out. For example, Japanese Patent Application Laid-open No. (Sho) 62-158490 discloses a process for preparing a ginseng tissue-cultivate having a high ginsenoside Rh content which comprises heat-treating the ginseng tissue-cultivate at a temperature of 110° to 160° C. However, it has the drawback that since the ginseng tissue-cultivate was used instead of ginseng as it is, the processed ginseng product has not a shape of an original ginseng and that tissue cultivate of the ginseng is different from the naturally cultivated original ginseng with respect to the various components and pharmacological effects [Korean Journal of Pharmacognosy 16, page 171 (1985)] and that the process is also complex and noneconomic due to the tissue-cultivating procedure. In addition, although a process wherein a ginseng was heat-treated at a high temperature was partially tried out, the process was merely employed in a process for manufacturing cosmetics or tea, and the study relating to the pharmacological effects of heat-treated ginseng was not carried out.

The inventors of the present invention have intensively carried out the scientific investigation concerning components and pharmacological effects of a ginseng, in particular a processing method of a ginseng and physiological activity of the processed ginseng. As a result of the investigation, the inventors have discovered that because the contents of the trace components present in a red ginseng are significantly increased as well as novel components are produced by heat-treating a ginseng, i.e., a fresh ginseng, a white ginseng or a fine root of ginseng, or an extract thereof at a very higher temperature than heat-treating temperature of a red ginseng, the pharmacological effects of the ginseng are substantially enhanced, and they have completed the present invention.

SUMMARY OF THE INVENTION

It is an object of the present invention to provide a processed ginseng product with enhanced pharmacological effects. In particular, it deals with a processed ginseng product in which a ratio of ginsenoside $(Rg_3+Rg_5)$ to $(Rc+Rd+Rb_1+Rb_2)$ is above 1.0.

It is an another object of the present invention to provide a drink composition containing the processed ginseng product.

These and other objects of the present invention can be achieved by heat-treating a ginseng at a high temperature of 120° to 180° C. for 0.5 to 20 hours.

BRIEF DESCRIPTION OF THE DRAWINGS

These and other features will become better understood with regard to the following description, appended claims and accompanying drawings where:

FIGS. 2(a), 2(b) and 2(c) show results of gas chromatogram of essential oil fractions from a fresh ginseng and from processed ginsengs which were heat-treated at a temperature of 120° C. for 2 hours and at a temperature of 150° C. for 2 hours, respectively.

DETAILED DESCRIPTION OF THE INVENTION

Figure 1:
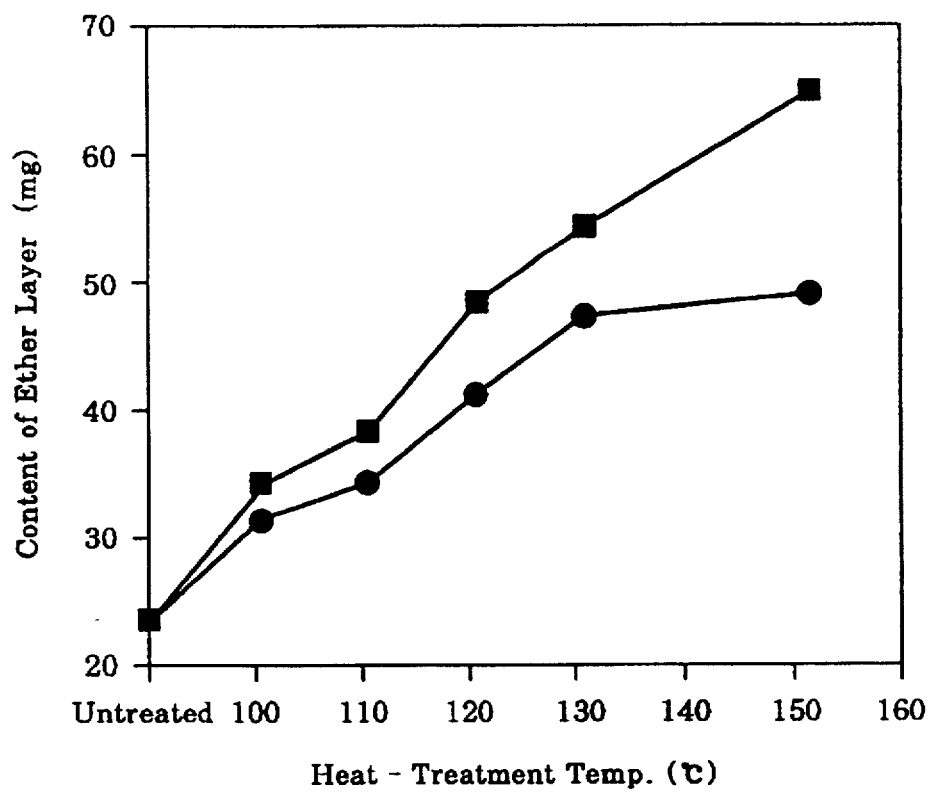
FIG. 1 is a graph showing changes in contents of essential oil fractions depending on the heat-treating condition (temperature and time) of a fresh ginseng.

In accordance with the present invention, a processed ginseng product which has enhanced pharmacological effects due to the increase in the pharmacological components caused by a heat-treatment at a high temperature is provided.

The ginseng which may be used herein include, but are not limited to, any one of a fresh ginseng, a white ginseng and a fine root of ginseng or ginseng leaves or extracts thereof, which can be used as it is, finely divided or powdered. In the present invention, Panax ginseng is generally employed, but Panax quinquefolium or Panax notoginseng may also be used.

In accordance with the present invention, a heat-treatment of a ginseng may be performed at a temperature of 120° to 180° C. for 0.5 to 20 hours, preferably at a temperature of 120° to 140° C. for 2 to 5 hours. The heating time varies depending on the heating temperature. The lower heating temperature requires the longer heating time. The heating procedure may be carried out by using a hot air, water vapor, nitrogen, helium, carbon dioxide or mixed gas thereof. In order to increase the efficiency, the heating process may be preferably performed in an airtight container such as autoclave. Alternatively, a small amount of water may be added to the container; otherwise, the ginseng may be preferably soaked in water and then heated in a closed container.

The ginseng thus processed may be dried at a lower temperature than the heating temperature of the preceding procedure, i.e., a normal temperature to 80° C., by a known manner to obtain a dried processed ginseng, or it may be further processed to obtain a powdered ginseng, if necessary.

Alternatively, the processed ginseng may be extracted using a known manner to obtain a processed ginseng extract. Specifically, the processed ginseng is extracted by using a solvent, and then the solvent is removed by concentrating or freeze-drying to obtain a processed ginseng extract as dried powders.

The solvent which may be employed herein includes a water, lower alcohol such as methanol, ethanol, etc., lower ketone such as acetone, methylethylketone, etc., supercritical fluid or mixed solvent thereof.

According to the present invention, the effect obtained by leaves of ginseng is comparable to that obtained by the ginseng as it is. Until now, the leaves of ginseng have been disused or been used as a livestock feed rather than as a medicinal use. Otherwise, only a portion of the leaves has been used as a raw material of cosmetics or food product. However, when an extract of leaves of ginseng is heat-treated in the same manner as in the present invention, a pharmacological effect is remarkably enhanced, so that extract can be used in already known uses of ginseng leaves as well as in medicinal use.

In accordance with the present process, an extract of processed ginseng may also be prepared by heat-treating in the same manner as described above while using an extract or an extract fraction of ginseng instead of a fresh ginseng, a white ginseng or a fine root of ginseng. In this case, because a ginseng extract is used, a volume of sample is diminished and thus an apparatus for processing the ginseng can be miniaturized. Thus, an energy required to heat the ginseng is reduced and heating conditions such as heating time and temperature, etc. can be more accurately modulated.

As mentioned above, the processed ginseng according to the present invention contains a large amount of various components, for example non-polar saponin compounds, phenolic compounds, polyacetylene compounds, etc., which are absent or present in a trace amount in a commercial fresh ginseng, white ginseng or red ginseng, so the processed ginseng has markedly enhanced pharmacological effects. Namely, various volatile components are produced by the heat-treating process of the ginseng. It is known that the volatile components exhibit antioxidant activity, anti-cancer activity, etc. Also, the processed ginseng of the present invention contains various saponin components, for example ginsenoside $Rg_3$, $Rg_5$, $Rh_1$, $Rh_2$, $Rh_3$, $Rh_4$, $F_4$, etc., which are absent or present in a trace amount in a commercial white ginseng or red ginseng. Among them, ginsenoside $F_4$, $Rg_3$, $Rg_5(\Delta20$, ginsenoside $Rg_3$) are present in large amounts. In particular, the processed ginseng product according to the present invention wherein a ratio of ginsenoside $(Rg_3+Rg_5)$ to $(Rc+Rd+Rb_1+Rb_2)$ is above 1.0 shows superior physiological activities as different from the prior processed ginseng product in which ginsenoside components such as $Rg_3$ and $Rg_5$ are hardly present.

Accordingly, it is possible to use the processed ginseng product which exhibits enhanced pharmacological effects by heat-treatment according to the present invention, i.e., powdered processed ginseng, processed ginseng extract, etc., as a raw material having a superior effectiveness to an original ginseng in a conventional use, for example, a variety of medicine agent, herbal medicine, health food, food product, tea, cosmetics, etc. The processed ginseng product according to the present invention is particularly useful in a drink composition.

In accordance with the present invention, a drink composition containing the processed ginseng product in the form of powder or extract is also provided. In the drink composition according to the present invention, a processed ginseng product in a dried state is generally contained in an amount of 200 to 2000 mg, preferably 400 to 1000 mg per one dose. If necessary, a drink composition according to the present invention contains an additional herbal drug extract, for example an extract of Zingiberis Rhizoma, Zizyphi Fructus, Cinnamoni Cortex, Lycii Fructus, Polygalae Radix, Astragali Radix, etc. A drink composition according to the present invention may also contain a conventional sweetener, flavor, preservative, etc.

DESCRIPTION OF THE PREFERRED EMBODIMENTS

The present invention will be illustrated in greater detail by way of the following examples and experimental examples. The examples are presented for illustration purpose only and should not be construed as limiting the invention, which is properly delineated in the claims.

EXAMPLE 1

1 kg of fine root of ginseng was placed into an autoclave and then was heated by steaming at 120° C. for 3 hours. The heat-treated fine root of ginseng was dried at 50° to 60° C. to obtain a desired processed ginseng.

EXAMPLE 2

1 kg of fresh ginseng(main root) was placed into an autoclave and then was heated by steaming at 130° C. for 2 hours. The heat-treated ginseng was dried at 50° to 60° C. to obtain a desired processed ginseng.

EXAMPLE 3

1 kg of dried fine root of ginseng was extracted with 2 liters of methanol under reflux in a water bath for 4 hours and then filtered to obtain a ginseng extract. The ginseng extract thus obtained was then dried under a reduced pressure. The ginseng extract obtained as syrup was placed into an autoclave and then was heated at 120° C. for 4 hours. The heat-treated ginseng extract was dried at 60° C. to obtain a processed ginseng extract as concentrated syrup.

EXAMPLE 4

The processed ginseng obtained in the above Example 1 was extracted with 2 liters of methanol under reflux in a water bath for 4 hours and then was filtered to obtain a ginseng extract. The ginseng extract thus obtained was then dried under a reduced pressure to obtain a powdered ginseng extract.

Experimental Example 1

Analysis of saponin components of processed ginseng according to the present invention 5 g of white ginseng and 5 ml of water were added to each of four 40 ml airtight stainless steel vessels and then were heated at 110° C. for 2 hours, at 120° C. for 2 hours and 3 hours, and at 130° C. for 2 hours, respectively. Each 5 g of the processed ginsengs thus obtained, of commercial white ginseng and of a commercial red ginseng was extracted 3 times with 100 ml of methanol, concentrated, suspended into water, and then extracted 3 times with 100 ml of ether. The resulting aqueous layers were extracted 3 times with 100 ml of butanol to obtain butanol fractions. The butanol fractions thus obtained were concentrated, dissolved in methanol and then analyzed using a HPLC (Column: LiChrosorb $NH_2$, mobile phase: $CH_3CN/H_2O$/i-PrOH=80/5/15→80/20/15. Detector: ELSD (Evaporative light scattering detector)). The results thus obtained are shown in Table 1 below.

TABLE 1

Relative Peak Area of Saponin Components of Ginseng

| Sample | $Rb_1$ | $Rb_2$ | Rc | Rd | $Rg_3$ | $Rg_5$ | $(Rg_3 + Rg_5)/$ $(Rc + Rd + Rb_1 + Rb_2)$ |
|---|---|---|---|---|---|---|---|
| 130° C./2 hrs | 4.06 | 3.44 | 3.98 | 3.82 | 21.00 | 16.17 | 2.43 |
| 120° C./3 hrs | 10.82 | 6.91 | 8.52 | 7.64 | 28.01 | 14.01 | 1.24 |
| 120° C./2 hrs | 10.46 | 7.74 | 10.66 | 5.58 | 24.12 | 11.35 | 1.03 |
| 110° C./2 hrs | 19.02 | 11.55 | 10.68 | 8.37 | 7.02 | 4.39 | 0.23 |
| White Ginseng | 22.15 | 3.25 | 5.86 | 2.47 | 0.00 | 0.00 | 0.00 |
| Red Ginseng | 30.11 | 9.69 | 12.45 | 1.76 | 1.05 | 1.05 | 0.01 |

As it can be seen from the results of above Table 1, heat-treated ginsengs according to the present invention contain remarkably increased ginseng saponin components $Rg_3$ and $Rg_5$ which are absent or present in a trace amount in a commercial white ginseng or red ginseng, so they exhibit superior pharmacological effects.

Further tests were undertaken to specifically identify the effects of heating temperature on the change in contents of saponin components, in particular ginsenoside $Rg_3$ and $Rg_5$. The ginsengs which were heat treated at 100°, 110°, 120°, 130°, 150°, 160°, 180° and 200° C. for 2 hours and a ginseng which was not heat-treated (fresh ginseng) were prepared. The contents of saponin components $Rg_3$ and $Rg_5$ of the ginsengs thus obtained were determined to confirm the change in contents of saponin components $Rg_3$ and $Rg_5$ due to a change in heating temperature. The results are shown in Table 2 below.

TABLE 2

Change in Contents of Ginsenoside $Rg_3$ and $Rg_5$ Due to a Change in heating temperature

| Ginsenoside | Untreated Ginseng (Fresh Ginseng) | Heating Temp. (°C.) Times (hrs) | | | | | | | |
|---|---|---|---|---|---|---|---|---|---|
| | | 100 (2) | 110 (2) | 120 (2) | 130 (2) | 150 (2) | 160 (2) | 180 (2) | 200 (2) |
| $Rg_3$ | 0.00 | 0.02 | 0.08 | 0.17 | 0.86 | 0.44 | 0.45 | 0.35 | 0.23 |
| $Rg_5$ | 0.00 | 0.02 | 0.05 | 0.08 | 0.44 | 0.53 | 0.56 | 0.48 | 0.38 |

Note) Contents of each components are expressed as % by weight based on the amount of a fresh ginseng.

The results show that the contents of ginsenoside $Rg_3$ and $Rg_5$ of ginseng which were heat-treated at 120° to 180° C.

significantly increased compared to that of a fresh ginseng (without heat-treatment) or a red ginseng (heat treating at 100° C.).

Meanwhile, when the ginseng is heat-treated at a high temperature of above 180° C., the contents of ginsenoside $Rg_3$ and $Rg_5$ are somewhat larger than that of a fresh ginseng. However, it is not desirable to heat the ginseng at a high temperature because special facility and excessive expense are required.

Experimental Example 2
Amount of Essential Oil Fraction According to the Heating Condition 10 vessels containing each 10 g of fresh ginsengs were divided into 2 groups of each 5 vessels. One group was heated at 100°, 110°, 120°, 130°, 150° C. for 2 hours, respectively, and the other group was heated at 100°, 110°, 120°, 130°, 150° C. for 4 hours, respectively. The heated ginsengs were extracted with 200 ml of methanol under reflux and the methanol was then removed by evaporation to obtain ginseng extracts. The extracts were suspended into the 100 ml of water, extracted 3 times with 100 ml of ether. The extracted ether fractions were collected and the solvent were removed by evaporation. The resultant essential oil components were weighed, and the changes in contents of essential oil fractions depending on the heating temperature and time were examined. The obtained results are shown in FIG. 1.

The essential oil fractions from the ginsengs contain phenolic components, polyacetylene compound. These components have been known as components having anti-oxidant activity, anti-cancer activity, etc.

The FIG. 1 shows that contents of essential oil fractions from the processed ginsengs according to the present invention were decidedly higher than that from the fresh ginseng which was not heat-treated and to that from a red ginseng which was heat-treated at 100° C. The result demonstrates the much stronger anti-oxidant activity and anti-cancer activity of processed ginsengs according to the present invention than those of a commercial fresh ginseng and red ginseng.

Experimental Example 3
Gas Chromatogram of Essential Oil Fraction from Processed Ginseng Each 10 g of fresh ginsengs was added to two airtight vessels and then was heated at 120° C. and at 150° C. for 2 hours, respectively. The heat-treated fresh ginsengs were extracted with 200 ml of methanol under reflux. The methanol were then removed by evaporation under a reduced pressure. The residues were suspended into 100 ml of water and then were extracted with 100 ml of ether. The ether fractions were concentrated to obtain essential oil fractions. The essential oil fractions thus obtained were dissolved in 2 ml of chloroform and were injected into the gas chromatography(GC) (Column: OV-1 25 m capillary column, Oven temperature: 170° C.→280° C., Detector: FID) in order to examine the essential oil fraction components. The essential oil fraction from the fresh ginseng which was not heat-treated was examined as described above. The results thus obtained are shown in FIG. 2.

The essential oil fractions from the ginsengs contained non-polar compound such as phenolic compounds, polyacetylene compound exhibiting anti-oxidant activity, age-resisting activity, anti-cancer activity, etc.

The FIG. 2(a) shows gas chromatogram obtained by the fresh ginseng which was not heat-treated. The FIGS. 2(b) and 2(c) show results of the gas chromatogram obtained by the ginsengs which were heat-treated at 120° C. for 2 hours and 150° C. for 2 hours, respectively.

The figures shows that the higher heating temperature makes a larger amount of non-polar components such as volatile essential oil components and polyacetylene compound. This result means that the ginseng which is heat-treated at a high temperature exhibits the more enhanced anti-oxidant activity due to the production of novel components.

Experimental Example 4
Anti-oxidant Activity of Processed Ginseng 5 g of white ginseng and 5 ml of water were added to each of three 40 ml airtight stainless steel vessels and then were heated at 110° C. for 2 hours and at 120° C. for 2 hours and 3 hours, respectively. The heat-treated white ginsengs were extracted with 200 ml of methanol under reflux and then were filtered. The methanol in filtrates thus obtained were removed by evaporation under a reduced pressure, and the residues were suspended into 100 ml of water and then were extracted 3 times with 100 ml of butanol saturated with water. The butanol fractions were concentrated under a reduced pressure to remove butanol, and the residues were then dissolved 20 ml of ethanol. The resultant solutions were diluted with ethanol in stepwise to prepare ½ dilute solution, ¼ dilute solution, ⅛ dilute solution, ¹⁄₁₆ dilute solution and ¹⁄₃₂ dilute solution as sample solution, respectively. Separately, control sample solutions were prepared as in the above method described with a white ginseng and a red ginseng which were not heat-treated.

0.1 ml of the sample solutions were added to each of the tubes, and 1.9 ml of 0.004% DPPH(diphenylpicrylhydrazyl) ethanol solutions were added thereto. These solutions were heated at a temperature of 37° C. for 30 min, and absorbance was determined at 515 nm. The results are shown in FIG. 3.

Figure 3:
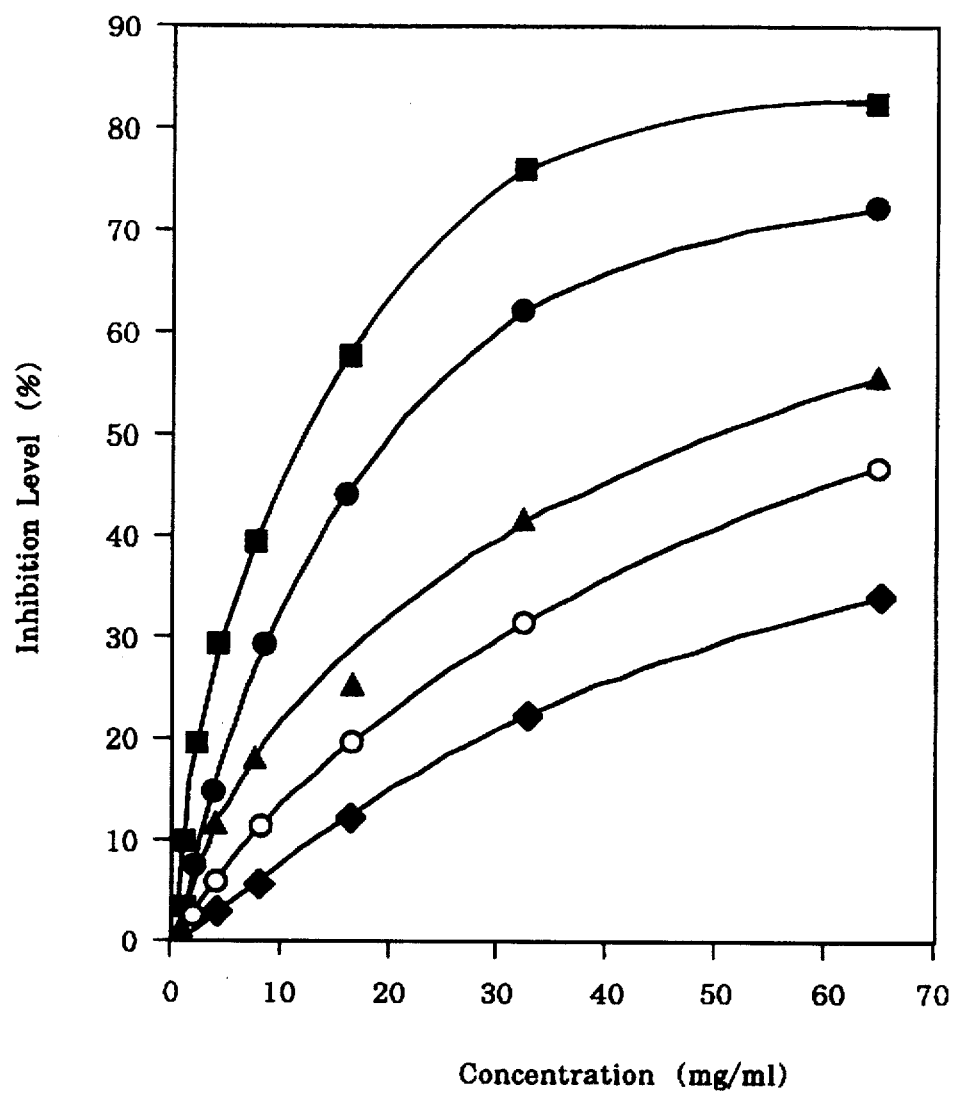
FIG. 3 is a graph comparing anti-oxidant activities of processed ginsengs according to the present invention which were heat-treated at 120° C. for 3 hours (-■-) and 120° C. for 2 hours (-●-) with those of an ginseng which was at 110° C. for 2 hours (-▲-), a commercial red ginseng (-○-) and white ginseng (-◆-) which were not heat-treated.

FIG. 3 shows that anti-oxidant activities of the ginseng extracts which were heat-treated at a high temperature, i.e., 120° C. according to the present invention were decidedly superior to that seen in the ginseng which was not heat-treated. For example, the anti-oxidant activity of the ginseng which was heat-treated at 120° C. for 3 hours was stronger about four fold than that of the ginseng which was heat-treated at 110° C. for 2 hours at 50% inhibition concentration. Such increase in anti-oxidant activity was dose-dependent.

It appears that the processed ginseng according to the present invention having a ratio of ginsenoside ($Rg_3$ +$Rg_5$) to ($Rc$+$Rd$+$Rb_1$+$Rb_2$) of above 1.0 is superior to the commercial white ginseng or red ginseng in view of the nutritive tonic effect.

Experimental Example 5
Vasodilation activity of extracts of processed ginseng according to the present invention Male Sprague-Dawley rats(300–400 g) were sacrificed and their thoracic aortae were removed and placed in a modified Krebs-Ringer bicarbonate solution containing(in mM): NaCl, 118.3; KCl, 4.7; $MgSO_4$, 1.2; $KH_2PO_4$, 1.2; $CaCl_2$, 2.5; $NaHCO_3$, 25.0; CaEDTA, 0.016; and glucose, 11.1 (control solution). The aortae were cleaned of loose connective tissue and then cut into eight rings(2–3 mm wide). In some rings, the endothelium was removed mechanically. The aortic rings were suspended horizontally between two stainless steel stirrups in organ chambers filled with 25 ml of control solution(37° C., pH 7.4) and bubbled with 95% $O_2$ and 5% $CO_2$. One of the stirrups was anchored to the organ chamber and one was connected to a transducer coupler (Narco bio-system) for the recording of isometric tension. The aortic rings were stretched progressively to the optimal tension (2 g) before the addition of phenylephrine ($10^{-6}M$). Once the plateau of the contraction to phenylephrine was obtained, the aortic rings were rinsed three times with warm (37° C.) control solution. After a resting period (30 min), the aortic rings were exposed again to phenylephrine ($10^{-6}M$). When the contraction had stabilized, acetylcholine ($10^{-6}$M) was added to test the presence or the absence of the endothelium. The organ chambers were rinsed three times with warm (37° C.) control solution before the addition of indomethacin($10^{-5}$M) to prevent the production of endogenous vasoactive prostanoids. A cumulative concentration-response curves to ginseng extracts were obtained following the contraction of aortic rings with phenylephrine($10^{-6}$M).

Figure 4:
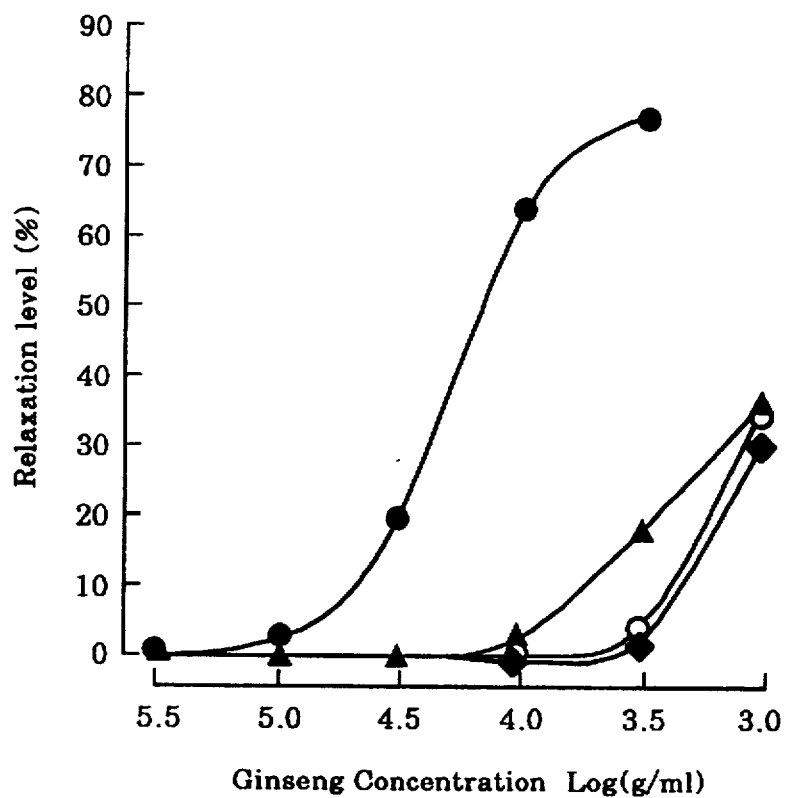
FIG. 4 is a graph comparing vasodilation activities of a processed ginseng according to the present invention which was heat-treated at 120° C. for 2 hours (-●-) with those of an ginseng which was heat-treated at 110° C. for 2 hours (-▲-), a red ginseng (-○-) and white ginseng (-♦-).

FIG. 4 shows the vasodilation effect of the ginseng extracts. As it can be seen from the results, although all ginseng extracts exhibited dose-dependent relaxation in aortae, a ginseng extract according to the present invention (120° C., 2 hours) exhibited activity even at a lower dose than prior ginseng extracts did. In particular, activity of the processed ginseng having a ratio of ginsenoside ($Rg_3+Rg_5$) to ($Rc+Rd+Rb_1+Rb_2$) of above 1.0 according to the present invention was stronger about 50 fold than that of the original white ginseng extract which was not heat-treated at 50% vasodilation concentration. The vasodilation effect of a processed ginseng was not observed in blood vessel from which endothelial cell is removed. Accordingly, it shows that the vasodilation activity of the processed ginseng in aorta is endothelium-dependent.

The results demonstrate the applicability of the processed ginseng as preventing or treating agent in diseases such as hypertension, arteriosclerosis, diabetes, sexual dysfunction due to circulatory disorder.

Composition Example

Composition Example 1

A drink composition containing the processed ginseng extracts according to the present invention having the following composition is prepared according to the invention by the process described herein:

| Composition | Contents (in 100 ml) |
| --- | --- |
| Processed ginseng extract | 360 mg |
| Zingiberis Rhizoma extract | 180 mg |
| Zizyphi Fructus extract | 1900 mg |
| Cinnamoni Cortex extract | 180 mg |
| Lycii Fructus extract | 200 mg |
| Taurine | 500 mg |
| Fructose | 10 g |
| Glucose | 0.5 g |
| Sucrose | 1 g |
| Citric acid | 200 mg |
| Sodium citrate | 100 mg |
| Sodium benzoate | 60 mg |
| Purified water | to 100 ml |

In accordance with the above composition, a purified water was added to a fructose, glucose and sucrose, heated to 95° C., and slowly cooled to 70° C. To the cooled solution, citric acid, sodium citrate and sodium benzoate were added with stirring, and then Zingiberis Rhizoma extract, Zizyphi Fructus extract, Cinnamoni Cortex extract, Lycii Fructus extract and Taurine were added with stirring to obtain a solution. To the resulting solution, the processed ginseng extract obtained in accordance with Example 4 was added and sufficiently stirred, and then purified water was added so as to give a drink composition of 100 ml containing 360 mg of processed ginseng extract.

Composition Example 2

| Composition | Contents (in 100 ml) |
| --- | --- |
| Processed ginseng extract | 600 mg |
| Zizyphi Fructus extract | 600 mg |
| Polygalae Radix extract | 300 mg |
| Cinnamoni Cortex extract | 200 mg |
| Taurine | 500 mg |
| Fructose | 10 g |
| Glucose | 0.5 g |
| Sucrose | 1 g |
| Citric acid | 200 mg |
| Sodium citrate | 100 mg |
| Sodium benzoate | 60 mg |
| Purified water | to 100 ml |

100 ml of a drink composition containing 600 mg of a processed ginseng extract was prepared in the similar manner with the Composition Example 1 using the above components.

What is claimed is:

1. A processed ginseng or processed ginseng extract comprising a ratio of ginsenoside ($Rg_3+Rg_5$) to ($Rc+Rd+Rb_1+Rb_2$) above 1.0, wherein said ginseng or ginseng extract is processed by heat-treating ginseng or an extract thereof at a temperature of 120° to 180° C. for 0.5 to 20 hours.

2. The processed ginseng or processed ginseng extract according to claim 1 wherein the raw material is a ginseng, ginseng leaves or ginseng extract.

3. The processed ginseng or processed ginseng extract according to claim 2 wherein the ginseng is a fresh ginseng, white ginseng or fine root of ginseng.

* * * * *